US00PP08008P

United States Patent [19]

Darnaud et al.

[11] Patent Number: Plant 8,008

[45] Date of Patent: Oct. 20, 1992

[54] NECTARINE TREE NAME PRITA

[76] Inventors: Jean-Pierre Darnaud, Route de Marseille, 26203 Montelimar Cedex; Jean Prim, Chemin St-Marc; Gabriel Tarte, Vieux Chemin d'Ille, both of Bouleternere, 66130 Ille-sur-Tet, all of France

[21] Appl. No.: 632,209

[22] Filed: Dec. 21, 1990

[51] Int. Cl.[5] ..... A01H 5/00

[52] U.S. Cl. ..... Plt./40.1

[58] Field of Search ..... Plt./40, 41

[56] References Cited

U.S. PATENT DOCUMENTS

P.P. 2,943 11/1969 Armstrong ..... Plt. 41

OTHER PUBLICATIONS

Brooks, R. M., et al., *Register of New Fruit and Nut Varieties* 1972, University of California Press, Berkeley, p. 296.

*Primary Examiner*—James R. Feyrer
*Attorney, Agent, or Firm*—Browdy and Neimark

[57] ABSTRACT

A new and distinct variety of nectarine tree, varietal name Prita, is a natural mutation of the bud of the Armking variety of nectarine. The new variety is characterized by its white fruit flesh and by its leaves which are whiter, especially the vein thereof, on the underside compared with Armking.

2 Drawing Sheets

This invention relates to a new and distinct variety of nectarine tree.

The new variety was discovered in 1984 by Jean-Pierre Darnaud, Jean Prim and Gabriel Tarte in their orchard of Armking variety nectarines in Boulternere 66, France. The new variety was found as a mutation on a branch on an Armking tree in the Prim's orchard, in Bouleternere 66, in the parcel No. 478/Section A—-Lieu-Dit "Les Maillols" by the three applicants.

The new variety, given the varietal name Prita, was reproduced asexually by Jean-Pierre Darnaud. The reproduction was accomplished by grafting on Persica Sylvestris in 1984. These trees exhibit the same characteristics as the mother tree.

DETAILED INFORMATION

TREE

Figure 1:
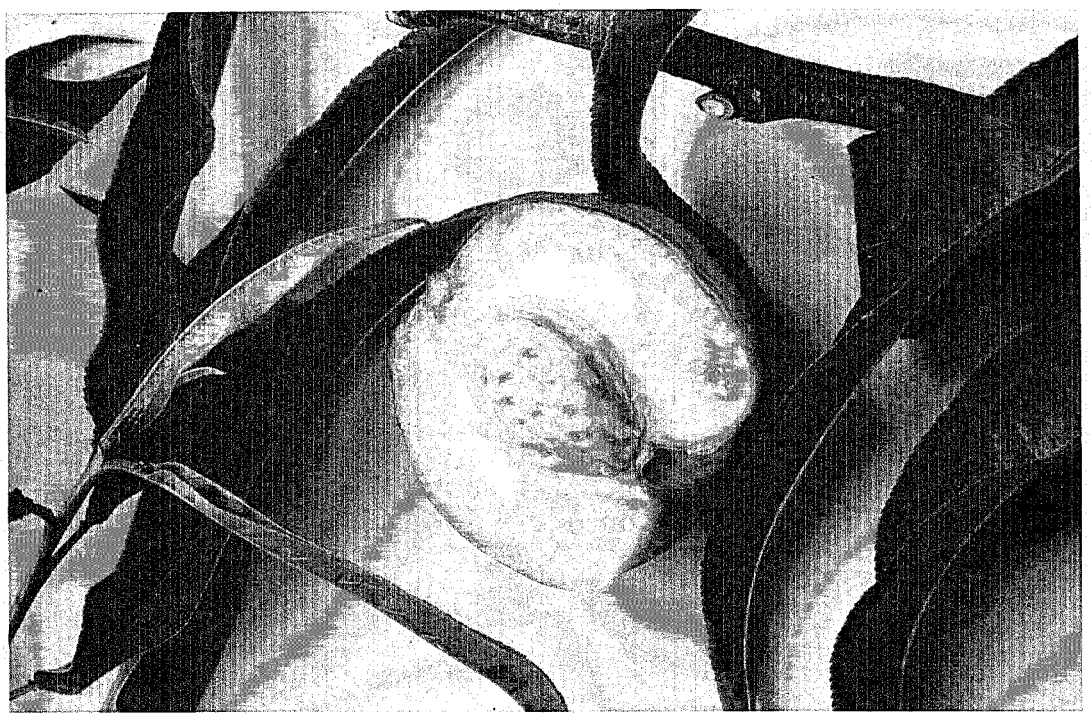
FIG. 1 shows a small branch, leaves and a longitudinal section of the fruit of the new variety showing the pit embedded in one half.
Figure 2:
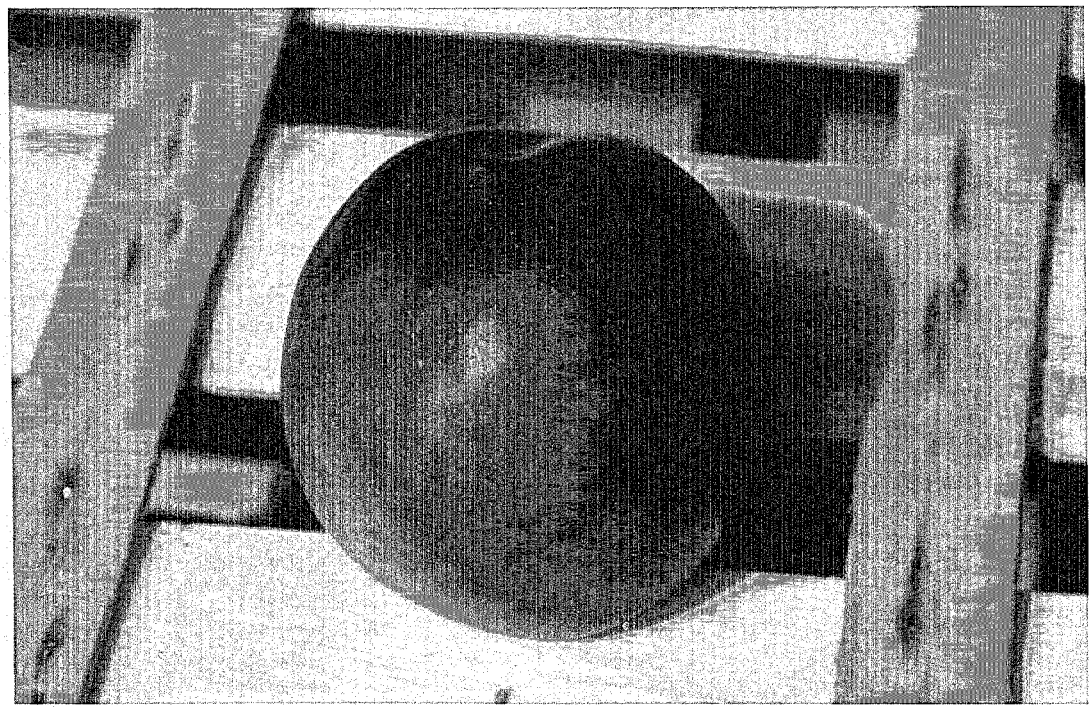
FIG. 2 shows the uncut fruit by itself.
Figure 3:
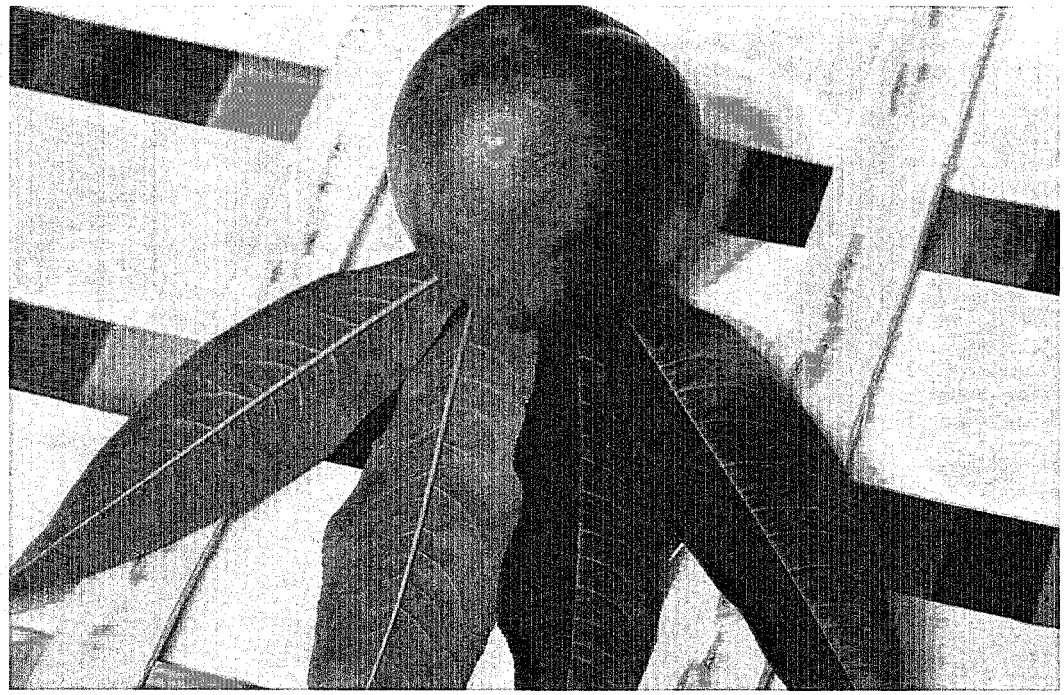
FIG. 3 shows the uncut fruit on a group of leaves as seen from underneath.
Figure 4:
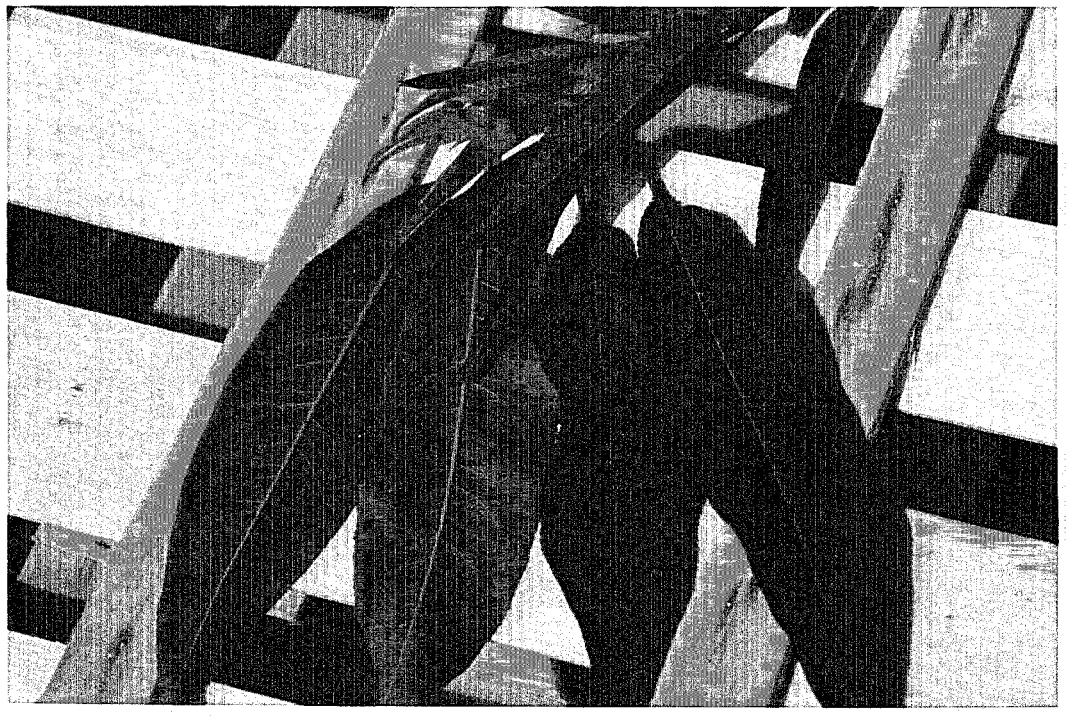
FIG. 4 shows a group of leaves as seen from underneath.

Habit: Vigorous; upright-spreading.

Chilling requirement: Moderate; from about equal to that of "Armking" to very slightly greater, as observed at Perpignan, France.

Fruit production: Heavy crop bearer.

Current growth:

*Surface texture.*—Smooth at first, with lenticels small and minute; with age, some larger, cracked, slightly raised lenticels appear toward the base of the more vigorous shoots.

*Color.*—Green at first, or reddish on exposed surfaces, with lenticels appearing as small, nearly white dots, all becoming more grown with age.

Two-year wood:

*Surface texture.*—Generally smooth, with slightly raised, irregular, longitudinal striations and numerous lenticels.

*Color.*—Brown.

Old wood:

*Surface texture.*—Generally smooth, with moderate number of large, raised lenticels, and some small, longitudinal fissures.

*Color.*—From grey to grayish-brown, or reddish-brown on more exposed surfaces.

Leaves:

*Size.*—Length: from 5½ inches to 7 inches. Width: from 1¼ inches to 1¾ inches.

*Shape.*—Lanceolate, with apex acuminate.

*Color (mature).*—Upper surface: Near Deep Dull White Green(1), Plate XXXII (R). Under surface: Near Chromium Green, Plate XXXII (R).

*Petiole.*—Medium length; from medium thickness to thick.

*Margin.*—Finely serrate; glandular.

*Glands.*—Mostly globose, but occasionally near reniform; medium size; usually 3 or 4, but sometimes 5 or 6 in number; borne both on the petiole and on the base of the blade.

Vegetative buds:

*Size.*—Small.

*Shape.*—Ovoid, unless compressed between flower buds.

*Scales.*—Thick pubescence; moderate length.

*Color.*—Dark brown.

FLOWERS

Dates of first and full bloom: Over a period of four years at Perpignan, France, first bloom varied from March 5 to March 11, and full bloom varied from March 5 to March 14.

Dormant flower buds:

*Shape.*—Ovoid.

*Scales.*—Pubescent.

*Color.*—Dark brown, with pubescence giving a whitish effect.

Open flower:

*Size.*—Single; usually 5 petals.
*Petalage.*—Single; usually 5 petals.
*Form.*—Cupped.
*Color.*—Dark pink.

FRUIT

Ripening dates: Generally ripens in early June at Perpignan, France over six years of observations, first ripening ranged from June 2 to June 15; ripens generally 5 days later, about 10 days to two weeks after "Springtime" peach, averaging about 12 days later.
Maturity when described: Hard-ripe.
Size: From medium to large for its season.
*Axial diameter.*—From 2¼ inches to 2½ inches.
*Transverse diameter in suture plane.*—From 2¼ inches to 2½ inches.
*Transverse diameter at right angles to suture plane.*—From 2¼ inches to 2½ inches.
Form: Relatively uniform; globose; sometimes slightly compressed laterally.
Suture: Straw Yellow; Generally shallow; extending from base to apex on ventral side; slight depression beyond pistil point.
Ventral surface: Rounded; usually lipped throughout; lips usually unequal.
Stem cavity: Usually rounded; sometimes slightly elongated in suture plane, with suture showing on one side.
*Depth.*—From ¼ inch to ⅜ inch.
*Width.*—From ¾ inch to 1 inch.
Base: From rounded to truncate.
Apex: Generally rounded; sometimes slight conical shape to end of fruit; pistil point insignificant.
Stem: From medium caliper to thick; glabrous; weak adherence to stone.
*Length.*—From about ¼ inch to ⅜ inch.
Skin:
*Thickness.*—From medium to thin.
*Texture.*—Medium.
*Tenacity to flesh.*—Free.
*Pubescence.*—None; characteristic smooth skin of the nectarine.
*Color.*—White with red coloring often mostly on one side and the other side being speckled, with the lighter ground color showing through, and the red coloring becoming particularly bright and glossy in effect right at tree-ripe stage, and more so in some years than in others.
Flesh:
*Quality.*—Medium firm; melting; fine texture.
*Aroma.*—Pronounced.
*Flavor.*—Distinctive nectarine flavor, with good balance between sugar and acid.
*Color.*—White with the surface of pit cavity straw yellow.
Stone:
*Tenacity of flesh.*—Basically free, but because of early ripening, stone adheres to flesh along both dorsal and ventral edges until the fruit is fully ripe, and to a slight extent on other surfaces.
*Size.*—From medium to large. Length: from about 1¼ inches to 1½ inches. Width: from about 1 inch to 1⅛ inches. Thickness: from about ¾ inch to ⅞ inch.
*Form.*—Ovoid.
*Base.*—Somewhat oblique.
*Hilum.*—Narrow and oblong.
*Apex.*—Acute.

*Sides.*—Only slightly unequal; curved on right and left sides; irregularly furrowed toward apex; pitted toward base.
*Ventral edge.*—Medium thickness; usually without wing toward base.
*Dorsal edge.*—Narrow; with shallow, narrow grove toward base; ridges on either side interrupted.
*Color.*—Between Vinaceous-Cinnamon, Plate XXIX (R) and Pinkish Cinnamon, Plate XXIX (R).

PLANT CHARACTERISTICS

The new variety of tree is of normal size, and the time of beginning of flowering is early. The flower shape is campanulate and the petal size is medium with a round petiole being present.

The color of the fruit is white and this is one of the characteristics of Prita which distinguishes it from its parent Armking. The stone adheres to the flesh, and the fruit matures early.

The new variety Prita also is differentiated from its parent Armking in the nature of its leaves which are characteristically more white on their under surface, especially the vein, than the leaves of its parent Armking.

In other respects the new variety Prita is similar to its parent Armking such as:

DISTINGUISHING TRAITS (1) A vigorous tree habit, with a size, volume and chilling requirement approximately that of "Armking" (U.S. Plant Pat. No. 2,943),
(2) The production of large crops of fruit of relatively large size and attractive appearance for fruit of such a ripening season as that of the new variety;
(3) A fruit ripening period which, on the average, is in the ripening season of "Armking" nectarine (U.S. Plant Pat. No. 2,943).
(4) Uniform fruit size, with a rounded to truncate fruit shape;
(5) An attractive fruit color, with a contrast of Yellow to Yellow ground color, heavily overlaid on one side with a red coloration which becomes particularly bright at the tree-ripe stage;
(6) Smooth fruit skin which is characteristic of the nectarine, without pubescence;
(7) White fruit flesh, with only a slight trace of red in the apical area when the fruit is tree-ripe;
(8) A tendency for the fruit flesh to cling to the stone to a slight degree until it is fully ripe, characteristic of early-ripening peaches and nectarines; and
(9) A distinctive and pleasing nectarine flavor, with a good balance between sugar and acid, better than "Armking."

The new variety Prita multiplies and reproduces faithfully by grafting.

Mr. Jean-Pierre Darnaud has applied for a French certificate of plant development for this new variety and was granted the number 05424 on Sep. 2, 1985.

We claim:

1. A new and distinct variety of nectarine tree substantially as herein shown, described, illustrated and identified, characterized by having a white flesh of the fruit instead of yellow flesh of its parent Armking and a whiter underside, especially the vein, of the leaves than its parent Armking.

* * * * *